(12) United States Patent
Chase (10) Patent No.: US 8,882,273 B2
(45) Date of Patent: Nov. 11, 2014

(54) NEUROCHROMATIC PRESCRIPTION DETERMINATION

(76) Inventor: Brad Lee Chase, Lakehead, CA (US)

( * ) Notice: Subject to any disclaimer, the term of this patent is extended or adjusted under 35 U.S.C. 154(b) by 46 days.

(21) Appl. No.: 13/368,149

(22) Filed: Feb. 7, 2012

(65) Prior Publication Data

US 2012/0249964 A1 Oct. 4, 2012

Related U.S. Application Data

(60) Provisional application No. 61/470,417, filed on Mar. 31, 2011.

(51) Int. Cl.
*A61B 3/02* (2006.01)
*A61B 3/00* (2006.01)
*A61B 3/113* (2006.01)

(52) U.S. Cl.
CPC .............. *A61B 3/113* (2013.01); *A61B 3/0025* (2013.01); *A61B 3/02* (2013.01); *A61B 3/00* (2013.01)
USPC ................. 351/210; 351/159.66; 351/159.73; 351/229; 351/233

(58) Field of Classification Search
USPC ............. 351/159.01, 159.24, 159.66, 159.73, 351/159.75–159.77, 210, 213, 216, 217, 351/222–227, 229, 230, 233–235, 246
See application file for complete search history.

(56) References Cited

U.S. PATENT DOCUMENTS

| | | | |
|---|---|---|---|
| 2,089,863 A * | 8/1937 | Updegrave | 351/203 |
| 3,672,780 A * | 6/1972 | Piringer | 356/425 |
| 3,879,113 A * | 4/1975 | Howland et al. | 351/206 |
| 5,042,937 A | 8/1991 | Cornsweet | |
| 5,339,151 A | 8/1994 | Shinn | |
| 5,528,431 A | 6/1996 | Wilkins | |
| 5,596,378 A * | 1/1997 | Kelman | 351/233 |
| 5,801,808 A | 9/1998 | Abraham et al. | |
| 6,099,126 A * | 8/2000 | Teskey | 351/213 |
| 6,145,984 A * | 11/2000 | Farwig | 351/49 |
| 7,372,640 B2 * | 5/2008 | Fung | 359/722 |
| 7,556,380 B2 | 7/2009 | Cohan et al. | |
| 7,568,799 B2 * | 8/2009 | Dreher et al. | 351/159.73 |

(Continued)

OTHER PUBLICATIONS

Defender Security Specification for Miniature PC Board Camera with Infrared Illumination, Part Number: 82-2995, download from http://www.mcmelectronics.com/contentiProductData/Catalog50/section15.pdf on Jul. 17, 2013.

(Continued)

*Primary Examiner* — Ricky Mack
*Assistant Examiner* — William Alexander (57) ABSTRACT

A method for determining a lens prescription for the eye. The method includes selecting a first ultraviolet (UV) trial lens and a second UV trial lens and determining whether the first UV trial lens or the second UV trial lens results in greater improvement in visual function. The second UV trial lens may be selected for the prescription when the second UV trial lens results in greater improvement in visual function as compared to the first UV trial lens. The method includes selecting a first color group comprising a first color trial lens and a second color trial lens and determining whether the first color trial lens or the second color trial lens results in greater improvement in visual function. The second color trial lens may be selected for the prescription when the second color trial lens results in greater improvement in visual function than the first color trial lens.

19 Claims, 5 Drawing Sheets

(56) References Cited

U.S. PATENT DOCUMENTS

| | | |
|---|---|---|
| 7,771,048 B2 * | 8/2010 | Dai et al. .................. 351/205 |
| 8,210,678 B1 * | 7/2012 | Farwig ................ 351/159.65 |
| 8,403,478 B2 * | 3/2013 | Ishak .................... 351/159.6 |
| 2002/0044254 A1 * | 4/2002 | Saathoff .................... 351/163 |
| 2003/0210378 A1 | 11/2003 | Riza |
| 2004/0046935 A1 | 3/2004 | Copland |
| 2004/0218142 A1 | 11/2004 | Wakil et al. |
| 2005/0104240 A1 * | 5/2005 | Jethmalani et al. ......... 264/1.38 |
| 2005/0213040 A1 | 9/2005 | Gross et al. |
| 2006/0092374 A1 * | 5/2006 | Ishak ........................ 351/159 |
| 2006/0170865 A1 | 8/2006 | Hirohara et al. |
| 2007/0195264 A1 | 8/2007 | Lai |
| 2008/0021298 A1 | 1/2008 | Cohan et al. |
| 2008/0143960 A1 * | 6/2008 | MacRae ..................... 351/230 |
| 2009/0262304 A1 * | 10/2009 | Dreher et al. .............. 351/233 |
| 2011/0178202 A1 * | 7/2011 | Laredo ....................... 523/107 |
| 2013/0077050 A1 * | 3/2013 | Chase ........................ 351/210 |

OTHER PUBLICATIONS

Kearns et al. Nov. 01, 2004, Springer, 32 (4), 463-476.

* cited by examiner

NEUROCHROMATIC PRESCRIPTION DETERMINATION

RELATED U.S. APPLICATIONS

This application claims the benefit of and priority to the copending provisional patent application Ser. No. 61/470,417, entitled "SYSTEMS AND METHODS FOR CHROMATIC VISION ENHANCEMENT," with filing date Mar. 31, 2011, and hereby incorporated by reference in its entirety.

This application is related to copending non-provisional patent application, Ser. No. 13/434,676, entitled "NEUROCHROMATIC TRIAL LENS KIT," with filing date Mar. 29, 2012, and hereby incorporated by reference in its entirety.

This application is related to copending non-provisional patent application, Ser. No. 13/434,558, entitled "NEUROCHROMATIC REFRACTOR," with filing date Mar. 29, 2012, and hereby incorporated by reference in its entirety

FIELD OF THE INVENTION

Embodiments of the present invention are generally related to vision enhancement, e.g., with the application of specialized and custom lenses for the eyes.

BACKGROUND OF THE INVENTION

Vision is one of the most important senses. People are in particular visual creatures, often favoring visual perception over other senses. Further, humans constantly use their eyes in almost every task whether it be for reading, walking, or driving. This reliance on the visual system as the primary sense for interacting with the world makes the human eye incredibly important and thereby meaning any deficiency in visual performance can have a large negative impact.

The eye and the visual processing system are quite complex and as such can be negatively impacted by a variety of conditions, syndromes, and complications. Such problems can result in photophobia, reduced field of vision, clarity of vision, and other visual compromises. While ophthalmic prescriptions are somewhat effective in reducing the negative effects of near-sightedness and far-sightedness, ophthalmic prescriptions and lenses are not able to solve or reduce a variety of conditions, syndromes, and complications. For example, ophthalmic lenses have limited effect on photophobia or reduced field of vision. Regular eye glasses mostly correct for image clarity and focus but do little to correct for other visual performance and acuity issues.

Thus, a need exists for a solution to alleviate visual system problems that are not solved or fully solved with current ophthalmic prescriptions and lenses.

SUMMARY OF THE INVENTION

Embodiments of the present invention medically and therapeutically treat or enhance the performance of the human visual experience by physician prescribed neurochromatic lenses. Embodiments of the present invention further provide effective treatment for the enhancement of vision and therapeutic treatment for a variety of neurovisual processing symptoms, anomalies, conditions, and syndromes.

Embodiments of the present invention are operable to improve a variety of various visual performance and visual function characteristics including improved visual acuity (e.g., more clear and enhanced visual perception of distant objects), improved visual field, enhanced visual saccade (e.g., eye movement across a page), increased contrast sensitivity, and increased recognition of color hues. Embodiments of the present invention are further operable to improve visual performance and visual function characteristics including increased eye coordination, increased pupil stabilization (e.g., stabilization of pupil shape to round), improved visual invoked response time (e.g., vision to action time), and improved blood flow in the brain which results in enhancement to cognitive response to visual cues. Embodiments of the present invention may make use of Neurochromatic© lens or trial lens available from NeuChroma Vision, Incorporated of Redding, Calif.

In one embodiment, the present invention is implemented as a method for determining a neurochromatic prescription. The method includes selecting a first ultraviolet (UV) trial lens and a second UV trial lens and determining whether the first UV trial lens or the second UV trial lens results in greater improvement in visual acuity. The second UV trial lens may then be selected for the neurochromatic prescription when the second UV trial lens results in greater improvement in visual acuity as compared to the first UV trial lens. The method further includes selecting a first color group comprising a first color trial lens and a second color trial lens and determining whether the first color trial lens or the second color trial lens results in greater improvement in visual acuity. The second color trial lens may then be selected for the neurochromatic prescription when the second color trial lens results in greater improvement in visual acuity as compared to the first color trial lens. Whether removal of the second UV trial lens results in an improvement in visual acuity may then be determined.

The method may further include selecting a first infrared (IR) trial lens and a second IR trial lens and determining whether the first IR trial lens or the second IR trial lens results in greater improvement in visual acuity. The second IR trial lens may then be selected for the neurochromatic prescription when the second IR trial lens results in greater improvement in visual acuity as compared to the first IR trial lens. In one embodiment, a camera operable to record the improvement in visual acuity is activated. The camera may be operable to record pupillary responses of a patient to trial lenses.

In one exemplary embodiment, the color group may comprise a third color trial lens and it may be determined whether the second color trial lens or the third color trial lens results in greater improvement in visual acuity. The third color trial lens may then be selected for the neurochromatic prescription when the third color trial lens results in greater improvement in visual acuity as compared to the second color trial lens. A second color group may be further selected which comprises a third color trial lens and a fourth color trial lens. A determination may then be made as to whether the third color trial lens or the fourth color trial lens results in greater improvement in visual acuity. The fourth color trial lens may then be selected for the neurochromatic prescription when the fourth color trial lens results in greater improvement in visual acuity as compared to the third color trial lens.

In one exemplary embodiment, after determining improvement in visual acuity with a plurality of color trial lenses from a plurality of color groups, the second UV trial lens may be reevaluated for improvement in visual acuity. In one embodiment, a full spectrum lighting element is activated to create a full spectrum lighting environment during the prescription process.

In one embodiment, the present invention is implemented as a method for selecting a color neurochromatic lens for a prescription. The method includes selecting a first color group comprising a plurality of color trial lenses and selecting a first color trial lens of the plurality of color trial lenses corresponding to a first frequency or wavelength of light. The first color group may be selected from the group consisting of red, orange, yellow, green, blue, indigo, and violet. The method further includes determining if there is a first improvement in visual acuity with the first color trial lens and in response to the first improvement in visual acuity, selecting a second color trial lens corresponding to a second frequency or wavelength of light. If there is a second improvement in visual acuity with the second color trial lens may then be determined. In response to the second improvement in visual acuity, the second color trial lens may be placed into a holding mechanism operable to hold a plurality of trial lenses. The second frequency or wavelength of light may then be recorded into the prescription. In response to not determining the second improvement in visual acuity, the first color trial lens may be placed into the holding mechanism and the corresponding frequency or wavelength added to the prescription. In response to not determining the first improvement in visual acuity, another color group may be selected.

The method may further include selecting a third color trial lens corresponding to a third frequency or wavelength of light in response to the second improvement in visual acuity. If there is a third improvement in visual acuity with the third color trial lens may then be determined. In response to the third improvement in visual acuity, the third color trial lens may then be placed into the holding mechanism. In response to not determining the third improvement in visual acuity, the second color trial lens may be placed into the holding mechanism. In one embodiment, the method may further include determining if there is a third improvement in visual acuity with the first color trial lens and the second color trial lens and in response to the third improvement in visual acuity, the first color trial lens and the second trial lens are placed into the holding mechanism. The corresponding frequencies or wavelengths for the first and second color trial lens may then be added to the prescription. The trial lenses (or corresponding frequencies or wavelengths) may then be added to the prescription.

In another embodiment, the present invention is implemented as a method for selecting a neurochromatic ultraviolet (UV) trial lens for a prescription. The method includes selecting a first UV trial lens of a plurality of UV trial lenses corresponding to a first frequency or wavelength and determining if there is a first improvement in visual acuity with the first UV trial lens. In response to the first improvement in visual acuity, a second UV trial lens corresponding to a second frequency of wavelength is selected. The method further includes determining if there is a second improvement in visual acuity with the second UV trial lens and in response to the second improvement in visual acuity, the second UV trial lens may be placed into a holding mechanism operable to hold a plurality of trial lenses. The second frequency or wavelength may then be recorded into the prescription. In response to not determining the second improvement in visual acuity, the first UV trial lens may be placed into the holding mechanism. In response to not determining the first improvement in visual acuity, a first color trial lens may be selected.

The method may further include selecting a third UV trial lens corresponding to a third frequency or wavelength in response to the second improvement in visual acuity and determining if there is a third improvement in visual acuity with the third UV trial lens. In response to the third improvement in visual acuity, the third UV trial lens may be placed into the holding mechanism. In response to not determining the third improvement in visual acuity, the second UV trial lens may be placed into the holding mechanism. In one embodiment, the method may further include determining if there is a third improvement in visual acuity with the first UV trial lens and the second UV trial lens and in response to the third improvement in visual acuity, the first color trial lens and the second trial lens may then be placed into the holding mechanism. The trial lenses (or corresponding frequencies or wavelengths) may then be added to the prescription.

BRIEF DESCRIPTION OF THE DRAWINGS

The present invention is illustrated by way of example, and not by way of limitation, in the figures of the accompanying drawings and in which like reference numerals refer to similar elements.

DETAILED DESCRIPTION OF THE INVENTION

Reference will now be made in detail to the preferred embodiments of the present invention, examples of which are illustrated in the accompanying drawings. While the invention will be described in conjunction with the preferred embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of embodiments of the present invention, numerous specific details are set forth in order to provide a thorough understanding of the present invention. However, it will be recognized by one of ordinary skill in the art that the present invention may be practiced without these specific details. In other instances, well-known methods, procedures, components, and circuits have not been described in detail as not to unnecessarily obscure aspects of the embodiments of the present invention.

Exemplary Methods of Neurochromatic Prescription

Figure 1:
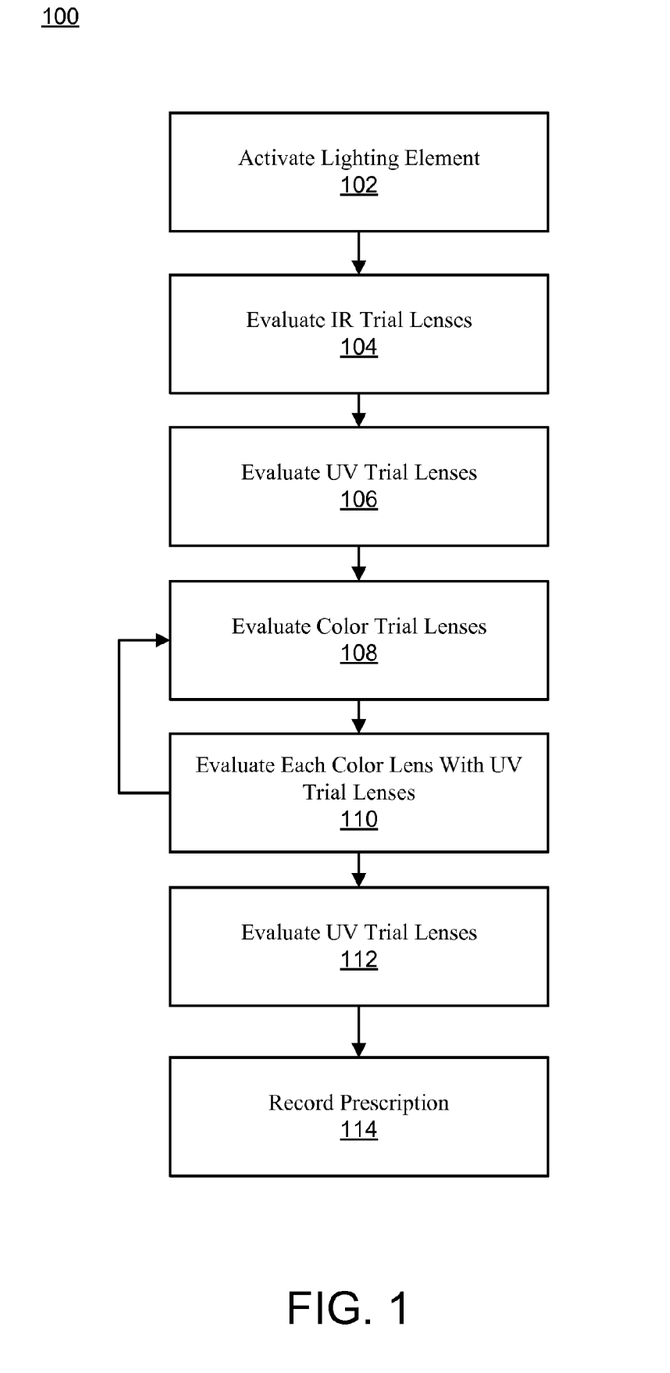
FIG. 1 shows a flowchart of an exemplary process for determining a neurochromatic prescription in accordance with an embodiment of the present invention.

FIG. 1 shows a flowchart of an exemplary process for determining a neurochromatic prescription in accordance with an embodiment of the present invention. Process 100 include evaluating each of a set of infrared (IR) trial lenses, ultraviolet (UV) trial lenses, and color trial lenses for resulting in improvements in visual performance and function. Embodiments of the present invention are operable to improve a variety of various visual performance and visual function characteristics including improved visual acuity (e.g., more clear and enhanced visual perception of distant objects), improved visual field, enhanced visual saccade (e.g., eye movement across a page), increased contrast sensitivity, and increased recognition of color hues. Embodiments of the present invention are further operable to improve visual performance and visual function characteristics including increased eye coordination, increased pupil stabilization (e.g., stabilization of pupil shape to round), improved visual invoked response time (e.g., vision to action time), and improved blood flow in the brain which results in enhancement to cognitive response to visual cues. The following terms may be trademarked or protected: neurochromatic and neurochromatic refraction.

In one embodiment, the improvement in visual performance and function substantially similar to the improvements in visual performance and function that ophthalmologists and optometrists look for. Embodiments of the present invention are operable for determination of a neurochromatic prescription resulting in neurological and physiological improvement. Embodiments of the present invention comprise a process for selecting a plurality of trial lenses, each corresponding to frequencies or wavelengths to be used in combination to create a prescription and a resultant lens to increase visual function (e.g., visual performance and visual function characteristics mentioned above).

For each trial lens, patients may be asked which trial lens results in the viewing object (e.g., near or far chart) being visually sharper, clearer, or more distinct. This will be paired with enhanced visual functions which may be measured in a variety of ways including: improved saccade, changes in visual field, increase in ability to perceive (e.g., increased ability to identify colors that would not otherwise be seen). For example, the patient may be asked whether the trial lens makes things clearer, bold, less blurry on the near or far chart. The physician may ask which lens is "most clear?" or "most focused?"

In one embodiment, process 100 is performed with use of a trial lens kit described in related copending non-provisional patent application, Ser. No 13/434,676, entitled "NEUROCHROMATIC TRIAL LENS KIT," with filing date Mar. 29, 2012, and hereby incorporated by reference in its entirety. In one embodiment, the trial lens kit is arranged so that the physician may move sequentially through the lenses. In one exemplary embodiment, the trial lens kit is setup to test IR trial lenses, color trial lenses, and then UV trial lenses.

At block 102, a lighting element is activated. In one embodiment, the lighting element is a full spectrum lighting element for creating a full spectrum lighting environment for a neurochromatic refractor.

At block 104, infrared (IR) trial lenses are evaluated for improvement in visual function. As described further herein, patients may be checked for a variety of conditions which indicate that the patients benefit from IR trial lens.

Patients with a traumatic brain injury, reduced levels of consciousness not induced by medications, cerebral hemorrhages, brain swelling, strokes, seizure disorders, migraines, ongoing and untreated chemical dependency of any substance, and severe auto-immune complex reaction often have an immediate reduction of symptoms and complications when introduced to infrared (IR) trial lenses or any other trial lenses (e.g., neurochromatic lens) or with an neurochromatic prescription. In one exemplary embodiment, IR lenses are the first choice due to increased probability of increased patient response. In one embodiment, such results occur when each or almost all of the available infrared trial lenses are used and prescribed. Generally, infrared trial lens are prescribed within the context of a neurochromatic prescription process for the purposes of either treating one of many neurovisual compromises or to enhance visual performance.

In one embodiment, if the patient's history or known dysfunction includes one of the above mentioned visually evoked phenomena, symptoms, or syndromes, it is recommended that the physician have available IR trial lenses for an aggressive and immediate therapeutic intervention. Patients having visually evoked or responses to light which either trigger or agitate the symptoms of a migraine, seizure, unexplained auto-immune responses, and withdrawal symptoms from chemical dependency may experience a reduction, if not cessation, of the symptoms and syndromes within 5-30 seconds of wearing a trial lens saturated to filter the maximum infrared.

It is noted that exposure to a neurochromatic trial lens may trigger any one of the symptoms or syndromes while exposure to any one of the trial lens may immediately halt, control, or diminish the visually evoked migraine, seizure, auto-immune complex response, and symptoms of mood altering drug withdrawal. The determining of the neurochromatic prescription may necessitate exposure to both types of trial lenses. Accordingly, the physician should have infrared trial lenses ready for such type of patients.

In one embodiment, should a patient have any of these dangerous neurovisual processing disorder caused conditions, syndromes, or complications, a physician should apply infrared trial lens to the patient. The complications, syndromes, headaches, seizures (tongue and tongue swallowing emergency responses should be ready), auto-immune and withdrawal symptoms may begin to reverse within approximately five seconds. Complete patient control and reversal of phenomenon might be likely regained within less than 30-60 seconds. The after-effects of those conditions, syndromes, conditions managed within less than five minutes from the applications of the infrared trial lenses.

At block 106, ultraviolet (UV) trial lenses are evaluated for improvement in visual performance and function. The UV trial lenses are evaluated to determine whether to include UV trial lens in the prescription. This may include determining the UV lens density or frequency or wavelength to be selected (e.g., process 200).

At block 108, color trial lenses are evaluated. This may include determinations of which color or hue of the color trial lenses to include in the prescription (e.g., process 300). In one embodiment, the color trial lenses are separated into color groups each having multiple lenses each corresponding to different frequencies or wavelengths or densities. In one exemplary embodiment, the color groups may include red, orange, yellow, green, blue, indigo, and violet. For example, each color group may have two #1 density lenses, one #2 density lens, and one #3 density lens. The two #1 density lenses may be used together for the patient's benefit when the patient does not benefit from a #2 density lens. The testing procedure for a color may include a #1 trial lens, #1 and #1 trial lenses, #2 trial lens, and #3 trial lens. The next color group may then be selected and tested. For example, if a blue lens is selected then each of the yellow lenses may be tested to determine which combination results in the greatest improvement in visual performance and function. It is appreciated that the use of each trial lens may remove a negative response of the human eye while increasing the body's response to the remaining transmitted light.

In one exemplary embodiment, each color group has two #1 density trial lenses, one #3 density trial lens, and one #5 density trial lens thereby allowing combinations of various density levels from 1-10.

At block 110, each color trial lens selected is evaluated with and without UV trial lenses. This evaluation may include determining whether to include a selected UV trial lens in combination with the color trial lens based on improvement of visual performance and function. In one embodiment, the UV trial lenses are introduced after a color trial lens is selected because the selected color trial lens may remove a portion of the UV light being transmitted. The evaluation of UV trial lenses may be performed for each color group.

It is noted that darker or lighter refers to how much light is being transmitted to the eye. Darker means there is more color and less light is transmitted to the eye across the entire spectrum. The frequency or wavelength of the color within each trial lens separates the lens from other lenses. In one embodiment, each color trial lens corresponds to a unique frequency or wavelength of light.

At block 112, UV trial lens are evaluated. The UV trial lens may be reevaluated for improvement in visual performance and function after one or more trial lenses are selected. In other words, consideration of the inclusion or exclusion of the UV trial lenses is undertaken.

At block 114, a prescription is recorded. The prescription may reflect the order of the IR, UV, and color trial lenses and thereby the densities or frequencies or wavelengths that result in visual improvement for the patient.

In one embodiment, the overall performance of photoreceptor cells at the retinal level is improved thereby changing the electrical signals going to the brain and changing blood flow. Embodiments of the present invention are operable to change the blood flow in the brain thereby resulting in measurable improvements in visual performance. Embodiments of the present invention are operable to adjust light received by the eyes which can result in beneficial changes in hormone response (e.g., seasonal effective disorder).

Embodiments of the present invention further facilitate increased visual acuity (e.g., more clear, bold, or distinct), increased visual field, enhanced visual saccade, increase contrast and sensitivity, increased recognition of visual color/hues, and increased blood flow resulting in enhanced cognitive response to visual queues. Embodiments of the present invention are operable determination of a resultant lens for increased utility of both eyes working coordinately (e.g., vortex of function and focus). For example, the eyes may not be seeing the same point resulting in some degree of reversal or dyslexia. This may create a perception that things are moving or going in and out of focus. The improvements facilitated by embodiments of the present invention can be measured with machines which determine where the pupils of both eyes are actually aiming.

Embodiments of the present invention are further operable to facilitate stabilization of the pupillary response to visual stimulation. For example, patients may have observable difficulty reading or during exposure to certain light which manifests as an abnormal shape or not round pupil. The abnormal shape of the pupil may cause the patient to experience eye fatigue, eye strain, and loss of place (e.g., while reading). Embodiments of the present invention can stabilize the pupillary response to result in a round pupil thereby enhancing other mechanical and neurophysical aspects of vision.

Embodiments of the present invention additionally facilitate enhanced visually evoked response time. For example, the time to blink when something comes toward your eye or time to shoot a weapon when something comes into your visual field may be lessened. In other words, embodiments of the present invention are operable to enhanced visual response time. Each of these improvements may be monitored during the trial lens (e.g., neurochromatic trial lens) selection process.

It is noted that some native populations have little trouble with near-sightedness or far-sightedness, stigmatism, etc. until they start to read because of how their eyes have been adapted over centuries. The problems may develop as a result of prolonged focused vision. Embodiments of the present invention are operable to provide treatment for problems that develop as a result of prolonged focused vision.

Neurochromatic prescriptions determined, as described herein, are operable for enhance visual performance and/or provide neurovisual therapeutic intervention therapy for the symptoms, syndromes, conditions, and anomalies exemplified within Table I. It is appreciated that neurochromatic lenses may provide enhanced visual performance and/or therapy for other symptoms, syndromes, conditions, and anomalies as well.

TABLE I

Exemplary symptoms, syndromes, conditions, and anomalies which neurochromatic lens provide relief 1  Visual and auditory dyslexia.
2  Blurred vision not fully corrected by ophthalmic lenses.
3  Contrast sensitivity compromises.
4  Color vision recognition compromises.
5  Restricted or compromised neurovisual fields of vision.
6  Convergence and divergence insufficiency.
7  Unilateral diplopia.
8  Compromises of night vision.
9  Wet and dry macular degeneration.
10 Visual aberrations and delusions not related to a psychotic or delusional condition.
11 Photophobia.
12 Visually evoked migraines.
13 Migraines characterized by aurora, photosensitivity, aberrations, dizziness, limited vision, or blindness.
14 Post migraines characterized by any one of the above.
15 Visually evoked seizure phenomena characterized by light stimulation or by any one of the above.
16 Post seizure activity characterized by any one of the above.
17 Cranial and brain hemorrhages.
18 Compromises of visual performance and cognitive awareness/alertness caused by blood blockage or hemorrhages (e.g., stroke) and/or traumatic brain injuries or post surgical trauma.
19 Some forms of schizophrenia or schizoid phenomena including delusional auditory and visually induced hallucination-type activities.
20 Reduction in autistic-type over stimulation of the visual and auditory kind.
21 Compromised saccade performance.
22 Irregular and inconsistent pupillary responses to light and focus activities.
23 Compromised cognitive performance not related to conditioned responses of learning or physical development.

TABLE I-continued

Exemplary symptoms, syndromes, conditions, and anomalies
which neurochromatic lens provide relief 24 Eye pain and strain related to visual performance.
25 Headaches related to visual pain or strain.
26 Neck and shoulder pain or distress related to visual stress.
27 Compromised reading speeds related to visual performance.
28 Compromised recall related to visual or auditory stimulation.
29 Non-migraine visually induced headaches, stress, or discomfort.
30 Seasonal affective disorder.
31 Computer vision syndrome.
32 Compromises in depth recognition and perception. For example, some patients cannot sustain a sight vocabulary or recognition of other visual data which appears to be a problem of either cognition, memory, or concentration of the neurovisual data that was heretofore already compromised.
33 Body coordination and physical performance requiring visual stimulation as one of several variables of perception.
34 Disorientation to space and motion.
35 Motion sickness.
36 Fear of heights.
37 Claustrophobia-type responses that cause a constriction and expansion of pupils seemingly consciously uncontrollable.
38 Some forms of general and specific anxiety disorders.
39 Physiologically related artistic performance.
40 Amblyopic (a.k.a. lazy eye) or wandering eye.
41 Excessive eye dominance.
42 Suppressive vision or visual performance of one eye not related to eye trauma, disease, or aging.
43 Specific photophobia related to lighting conditions, working environments, tasks, seasons of the year, or tools.
44 Post surgical photophobia.
45 Post traumatic brain injuries independent of hemorrhages or not.
46 Post traumatic stress disorders or syndromes.
47 Post concussion hyper-light sensitivity.
48 Compromised night vision.
49 Hyper-sensitive night or storm-type related vision compromises.
50 Myopia phenomena.
51 Astigmatism phenomena.
52 Strabismus phenomena.
53 "Comfort" or "performance" (e.g., +0.25 to +0.50) ophthalmic prescriptions.
54 Pharmaceutical prescription induced photophobia, e.g., caused by most hormonal based medications such as birth control or menopausal prescriptions.
55 Compromises in spatial differentiation.
56 Disparity between reading, writing, or mathematic capabilities as to any or all of these related to kinesthetic and/or mechanical aptitude.
57 Visual comprehension enhanced by "hearing the words" inside one's head or by reading out-loud to process fully.
58 The use of a finger or any other kind of marker or place keeper to read and maintain proper tracking.
59 High end near-sighted prescriptions.
60 Patients suffering from minor to severe depression (e.g., situational to needs of chronic dimness or brightness of light).
61 Lacking in physical coordination or clumsiness.
62 Premature fatigue or sleepiness with prolonged visual tasks including and not limited to driving, reading, sewing, sightseeing.
63 Nausea or upset stomach with visual tasks.
64 Abnormal pupillary sizes and shapes not related to bright or darkness.
65 Patients who experience "glare" or excessive brightness in normal lighting conditions and situations.
66 Patients who cannot drive at night or in stormy conditions because of failed or compromised vision.
67 Patients who report a "smudged" or "fogged" vision where upon a physiological examination there are no known causal factors.
68 Patients who report visual aberrations such as letters or words moving, switching, disappearing, fading away, changing size or shape, having a glow or luminance around print or coming from the background of the print. These and other dyslexic symptoms are known to respond to a neurochromatic lens.
69 Patients who see a white background on the printed page, from art, as having a color or hue, or glare.
70 Patients who see night lighting such as street lights, vehicle lights as having a color or hue, streaks, or having an abnormal comfort or affect.
71 Patients affected by chronic and severe fevers.
72 Patients affected by Down Syndrome.
73 Patients with compromises in cognitive function caused by disease, accident, or trauma.
74 Patients with varied degenerative muscular diseases.
75 Patients affected with chronic fatigue syndrome.
76 Limited or narrow band of light spectrum photophobia.
77 Major depression not identified as seasonal affective disorder.
78 Post traumatic stress disorder visually evoked symptoms.

TABLE I-continued

Exemplary symptoms, syndromes, conditions, and anomalies
which neurochromatic lens provide relief 79 Patients who complain or say there is excessive glare or aberrations abound the words and images of printed material.
80 Patients who complain or say there never is enough light to read comfortably or effectively.
81 Patients identified as having retinal pigmatosa, Graves' disease, chromic fatigue syndrome, degenerative muscle diseases of varied sorts, connective tissue diseases of varied sorts, lupus patients, other auto-immune diseased or compromised patients, patients having chemo or radiation therapies.
82 Patients with albinoism.
83 Compromised visually evoked responses.
84 Situational visual compromise or visual difficulties.

Figure 2:
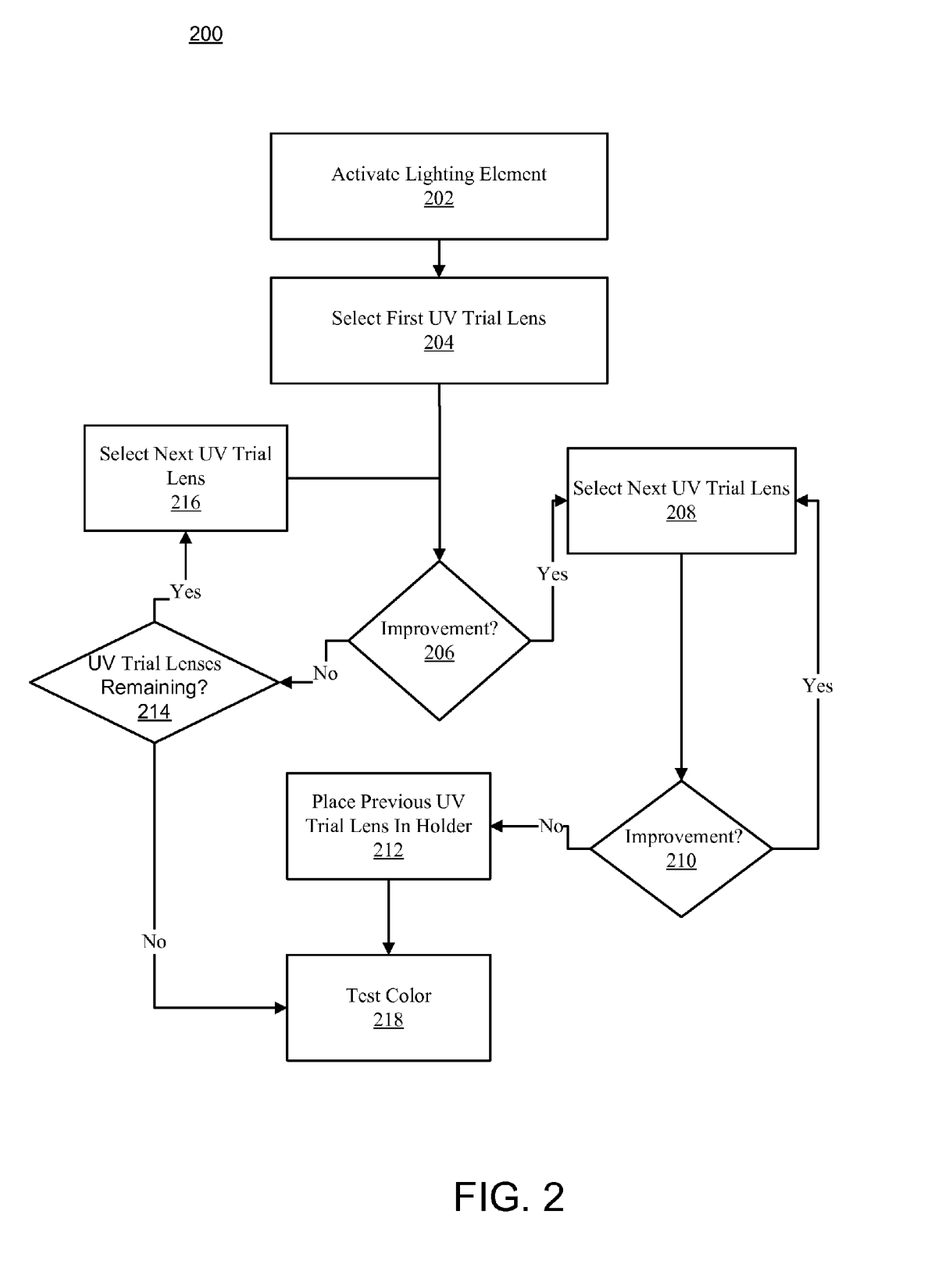
FIG. 2 shows a flowchart of an exemplary process for selection of an ultraviolet (UV) trial lens in accordance with an embodiment of the present invention.

FIG. 2 shows a flowchart of an exemplary process for selection of an ultraviolet (UV) trial lens in accordance with an embodiment of the present invention. Process 200 may be performed by a physician (e.g., optometrist or ophthalmologist) to select an UV lens for a neurochromatic prescription.

At block 202, a lighting element is activated. In one embodiment, the light element may be full spectrum light operable for use in creating a full spectrum lighting environment. The lighting element may be a full room testing light. It is noted that without an appropriate lighting element diagnoses and neurochromatic prescriptions may be negatively impacted.

It is appreciated that testing and prescribing of neurochromatic lenses may necessitate a specific exposure to specific light where the patient experiences compromised visual performance and corresponding symptoms (e.g., headaches or eye strain). Common causes may be environmental, vocational, or sports related (e.g., glare in a baseball field, under light lights, "that time of day," or using equipment during a dental hygienic cleaning).

Generally speaking, patients are exposed to each of the lowest density or the lightest color (e.g., #1 of each of the group of colors or tinted neurochromatic lenses). Each trial lens maybe be inserted by the physician into the sliding tray of a refractor device (e.g., neurochromatic refractor) and compared with another lens of another color or same color just as two lenses would be compared in a standard ophthalmic refractive process in eye examinations. A patient observes an object selected and determined by a physician. In one embodiment, the same object will be used throughout the entire examination. The physician may then determine which of the trial lenses makes the object observed the most in focus, most clear, and easiest to see for the patient.

In one embodiment, the order in which lens (e.g., UV and color lens) are selected is maintained during the prescription determination process. Close attention to the order the lens are prescribed is maintained because lens from the prescription will be manufactured according to the ordering in the prescription. For example, the first lens selected will be farthest from the patient's eye and each successive lens will be closer to the patient's eyes.

The prescription reflects the order in which the trial lenses are within the selected tray during the prescription process. In one embodiment, the neurochromatic refractor device and neurochromatic refractive prescriptions can accommodate up to six trial lenses which are incorporated and ordered by the physician to manufacture a single eyewear prescription. For example, the first chosen lens will be placed furthest from the eyes. In one exemplary embodiment, the neurochromatic refractor device may accommodate up to seven trial lens (e.g., six color lenses and one UV lens).

Figure 3:
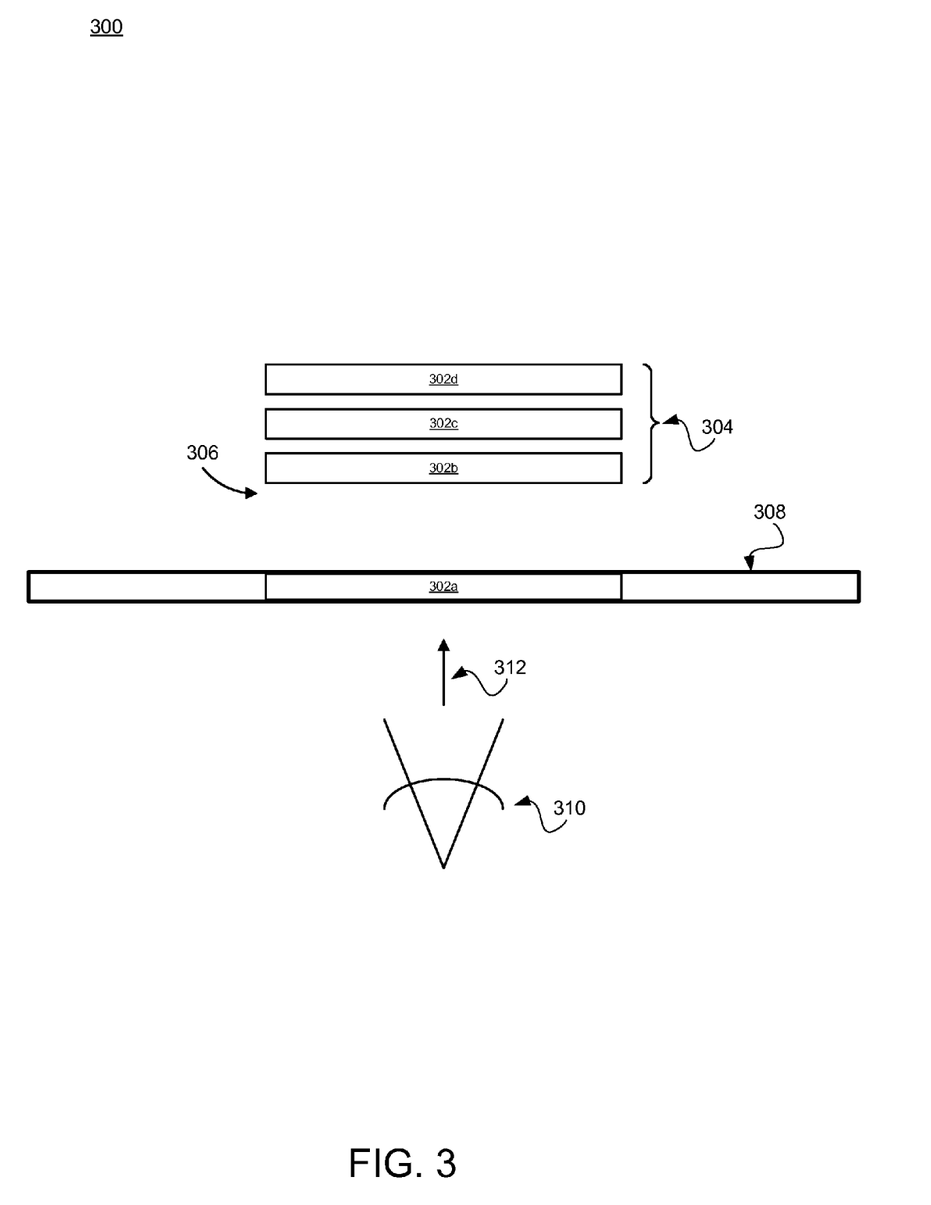
FIG. 3 shows a diagram of an exemplary configuration of selected trial lenses and a trial lens being tested in accordance with an embodiment of the present invention.

Referring to FIG. 3, FIG. 3 shows a diagram of an exemplary configuration of selected trial lenses and a trial lens being tested in accordance with an embodiment of the present invention. Diagram 300 includes trial lenses 302a-d, patient's eye 310, and slide channel 308. Slide channel 308 may be part a refractor device, as described below, and facilitates testing of trial lens 302a by allowing trial lens 302a to be brought in and out of the patient's line of sight 312.

Selected trial lenses 304 include trial lenses 302b-d which have been selected on the basis improving the visual performance and visual function of the patient. In one embodiment, as each trial lens is selected, the selected trial lens is placed in front of the previously selected lenses. For example, if trial lens 302 is selected, trial lens 302 will be placed in position 306 in front of selected trial lens 304. As shown in diagram 300, trial lens 302d was selected before trial lens 302c which was selected before trial lens 302b.

In one embodiment, the UV lens is maintained in a position farthest from the patient's eyes during the prescription process. During the prescription process if an UV trial lens is rejected in the first round of the neurochromatic refraction prescription process, the UV trial lens may be reintroduced after each of the other trial lenses (e.g., color trial lenses) have been rejected. Each of the UV trial lenses may be reintroduced at the outermost distance away from the eyes.

The prescription process may be competed with use of a neurochromatic refractor device as described in related copending non-provisional patent application, Ser. No. 13/434,558, entitled "NEUROCHROMATIC REFRACTOR," with filing date Mar. 29, 2012. The other trial lenses (e.g., non-UV) may be positioned in the refractor device in the order the lenses are prescribed with the first lens being farthest away from the patient's eyes and the last prescribed trial lens being closest to the patient's eyes.

It is appreciated that for accurate neurochromatic prescriptions, patients should wear their ophthalmic prescription during the neurochromatic refractive process. It is appreciated that if a patient wears a tinted lens, an anti-glare reflective lens, an ultraviolet coated lens, a progressively darkening lens (e.g., Corning Photo-Grey lenses), Transition lenses, or polarized lenses, the prescription process may be negatively impacted. In one embodiment, patients with contacts should wear them during the neurochromatic prescription process. The contact prescription should be free of any tint, which may introduce error into the neurochromatic prescription process.

Patients with surgically implanted artificial lens which have 100% UV protection need not be exposed to the UV trial lenses. This is also true for patients having ophthalmic prescriptions that already have an UV coating. Accordingly, the presence or non-presence of an UV coating may be determined prior to the neurochromatic prescription process.

The addition of an UV trial lens is anticipated to be about 50%. It is appreciated that the restriction of transmission of some UV light through a plastic lens is already inhibited by absorbing and distillation of the UV frequency within the plastic lens itself. Consequently, only some patients may require further reductions of the UV frequency.

Referring back to FIG. 2, at block 204, a first UV trial lens is selected. In one embodiment, a pre-selected lowest density UV trial lens (e.g., UV #1) is placed into a neurochromatic refractor in such fashion that a patient may view through the UV trial lens at a near-point reading object or a far-point eye chart. The objective being to improve or enhance the visual clarity, acuity, or functional sight by having the patient look through the UV trial lens. The exact line or object of either the near or far point eye chart may be designed by the physician. The physician may then direct and ask the patient to follow the physician's instructions and comment upon the visual clarity or acuity with and without the patient viewing the selected object through the UV neurochromatic trial lens.

At block 206, whether there is an improvement in visual function is determined. Based on subjective and existential reporting of the patient, determination of the visual clarity or performance and function may be determined. The physician may easily measure and confirm what the patient has reported using the physician's standards applicable during routine eye or ophthalmic examinations. In one embodiment, a camera may be used to record the neurochromatic prescription process. The camera may be attached or coupled to a photopter and/or a neurochromatic refractor. The camera allows the physician to observe and record pupillary responses and thereby determine the most proper trial lens or lenses (e.g., neurochromatic lenses). The camera allows recording of prescription process in accordance with external examination determinations subsequent to approval of specific neurochromatic CPT (Common Physician Terminology) and IDC (International code of Diagnostic) codes.

The camera allows monitoring of the pupillary response and determining whether the pupil shape has responded to the trial lens. The camera thereby allows assessment, diagnosis, and treatment for pupillary conditions. For example, the camera allows watching for a normalized pupillary response which occurs with stabilized and enhanced vision. The camera further allows monitoring of pupil movement to determine which trial lenses are more effective, which show poor pupil movement, and which show good pupil movement. It is appreciated that monitoring the patient's pupillary response provided a cross check to determine whether the patient's response is objective or subjective. In one exemplary embodiment, the camera is used to record a time tagged movie of the patient's responses to the trial lens which may be stored on a computer.

The physician may observe the patient taking into account both the ease upon which, and the time allotted to sustain and maintain focus with and without the UV trial lens. The physician may further take into account the variety of pupillary reactions including both size and shape of the patient's pupil denoting consistency of a uniform pupillary response eye-to-eye and uniform circular shape corresponding to and consistent with normal versus abnormal or statistically infrequent pupillary responses to a fixed object of focus. Observation of pupillary response may be done via physician observation or by using a camera attached to an arm of a neurochromatic refractor.

If the patient reports back either an improvement or enhancement of visual clarity or performance and function with the UV trial lens versus viewing the object without the UV trial lens then the UV trial lens is selected over no UV trial lens. The patient's reporting of an improvement of, or an enhancement with the UV trial lens should correspond with the physician's observation that the patient's ease of focus and pupillary responses are more normalized when viewing through the UV trial lens. If the patient and the physician are unable to evoke a positive improvement of visual function or performance, the UV trial lens should not be selected or chosen. If there is an improvement, block 208 is performed. If there is no improvement, block 214 is performed.

At block 208, the next UV trial lens is selected. If the patient has selected the initial UV trial lens (e.g., UV trial lens #1), then the physician selects the next highest density of the UV scale (e.g., UV trial lens #2) for comparison against the initially selected UV trial lens. In one embodiment, using a routine refraction of either plus or minus ophthalmic lenses the physician and patient may either select or reject UV trial lens #1 or #2.

At block 210, whether there is an improvement in visual function is determined. If there is not an improvement, block 212 is performed. If there is an improvement block 208 is performed. If the patient has selected UV trial lens #2, then UV trial lens #2 may be compared against UV trial lens #3. It is appreciated that additional levels of increasing density of UV trial lens may be tested and embodiments of the present invention are not intended to be limited to the exemplary discussion of three UV trial lens (e.g., #1-3).

At block 212, the previous UV trial lens that resulted in improvement in visual function is placed in a holding mechanism. For example, if the patient has rejected UV trial lens #2 and favors UV trial lens #1, then the UV trial lens #1 is selected to remain in the neurochromatic refractor's sliding tray. Whichever of the UV trial lens selected (e.g., resulting in improved visual acuity) is placed into the holding mechanism (e.g., tray) of the neurochromatic refractor and subsequently compared with the rest of the trial lenses (e.g., tinted or colored trial lenses).

At block 214, whether there are any remaining UV trial lenses to be tested is determined. If the patient has rejected UV trial lens #1, the physician will compare the patient's vision with UV trial lens #2 and #3 by placement and viewing via the neurochromatic refractor's hold-sliding tray for comparative analysis, rejection, or selection (e.g., via blocks 216 and 206). At block 216, the next UV trial lens is selected.

At block 218, color trial lens are evaluated or tested. The color trial lens may be tested as described with respect to FIG. 4.

Figure 4:
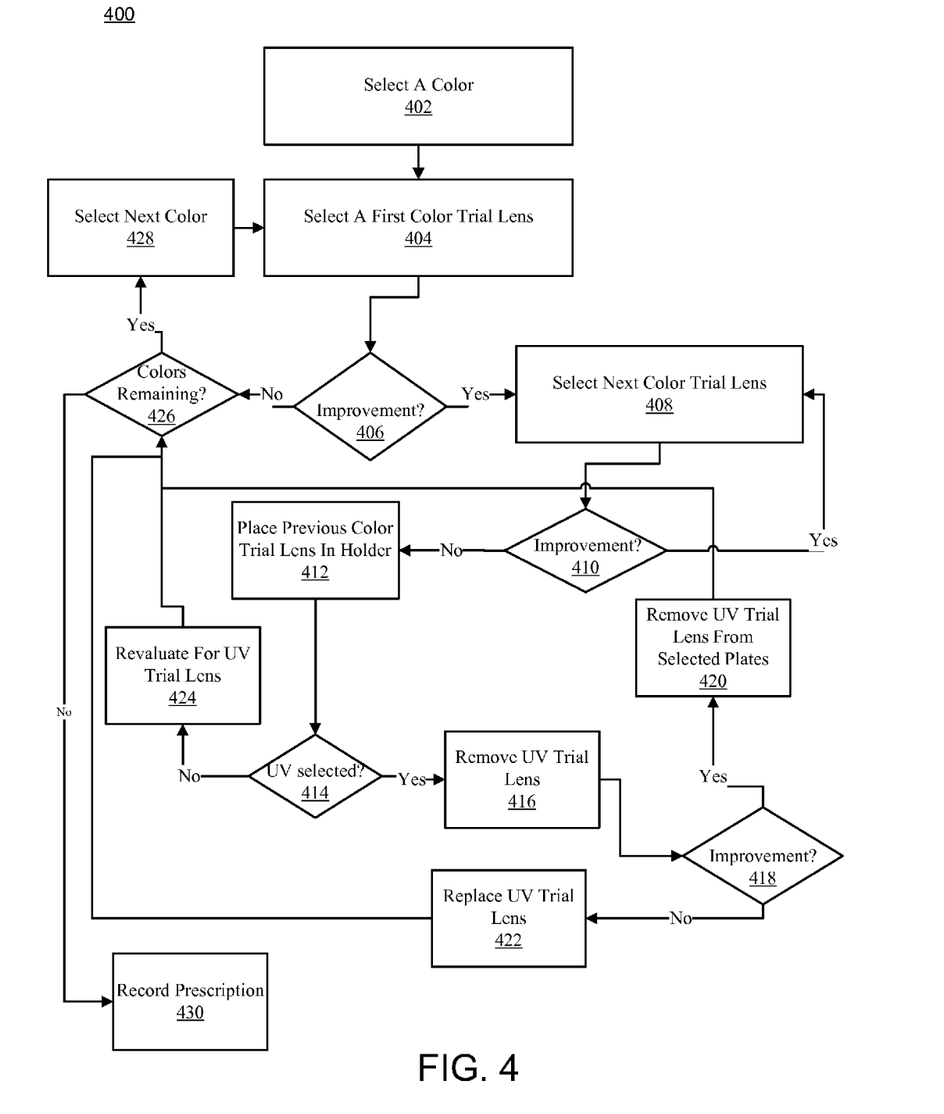
FIG. 4 shows a flowchart of an exemplary process for selecting one or more color lens in accordance with an embodiment of the present invention.

FIG. 4 shows a flowchart of an exemplary process for selecting one or more color trial lenses in accordance with an embodiment of the present invention. Process 400 may be performed by a physician (e.g., optometrist or ophthalmologist) to select one or more color trial lenses for a neurochromatic prescription. Process 400 may be performed whether or not a patient has selected an UV trial lens. A physician may expose the patient to color trial lenses starting with the lightest color, hue, or density of each of the colors present in a trial lens kit. The lowest density of each color trial lens may be marked or labeled #1 and each increasingly dense trial lens may be marked with a #2, #3, etc. For example, a blue colored or tinted trial lens may be identified as "BL 1," "BL 2," and "BL 3."

In one exemplary embodiment, the #1 lens is the lightest lens, #2 lens is next darkest, and #3 is the darkest. In one embodiment, process 400 is performed starting with the lightest lens for each color and then subsequent lenses which are increasingly dark. Increasingly dark lenses may thus be tried while improvements are observed and when a trial lens just results in increased darkness (e.g., casting a shadow or a sun glass effect), trial lens selection is made of the previous trial lens resulting in improvement in visual function. It is appreciated that a #1 lens may not be half as dark as a #2 lens. For example, a yellow #1 lens may be a very light yellow that may be hardly noticeable while a yellow #2 lens may have a tint substantially similar to a yellow traffic sign. It is noted that the different densities correspond to different frequencies or wavelengths that the trial lenses transmit.

At block 402, a color is selected. The color may be selected based on pathology of a patient or based on an ordering of a lens trial kit (e.g., color groups). In one embodiment, the basic colors are tested first.

At block 404, a first color trial lens is selected. In one embodiment, the first color trial lens selected has the lowest density for the selected color. For example, it may be the lowest density blue trial lens of the trial lens kit (e.g., blue #1).

At block 406, whether there is an improvement in visual function is determined. If there is an improvement block 408 is performed. If there is not an improvement, block 426 is performed.

As the physician exposes the patient to each of lightest color or lowest density of the trial lenses, the physician observes the patient taking into account both the ease upon which and the time allotted to sustain and maintain focus with each of the trial lenses. The physician may also take into account both the size and shape of the patient's pupils denoting consistency of a uniform pupillary response eye-to-eye and uniform circular shape corresponding to normal versus abnormal pupillary responses to a fixed object of focus.

At block 408, the next color trial lens is selected. As the prescriptive process is performed, each density of the selected color of the trial lenses is tested against the other trial lenses for the selected color. For example, a blue #1 trial lens is compared with a blue #2 trial lens. If the #2 trial lens is selected over a #1 trial lens, then the #2 trial lens is compared with a #3 trial lens. The same clinical and visual criteria for the trial lens selection is to be maintained by the prescribing physician as during an ophthalmic prescription.

At block 410, whether there is an improvement in visual function is determined. If the patient reports either an improvement of visual function or an enhancement of visual clarity or performance and function with the trial lens versus viewing the same object without the color trial lens, then the trial lens is selected. If there is an improvement, block 408 is performed. If there is not an improvement, block 412 is performed.

At block 412, the previous color trial lens is placed in a holding mechanism. If the patient's visual criteria is either improved or enhanced and the patient sees a color or any through the lens as a tint, then the darker or denser trial lens has been over-prescribed. Then the lower density trial lens with an observable improvement and without the perceived tint is selected. The selected lens is placed in the holding rack of the refractive device closest to the patient's eyes. If an UV trial lens was previously selected, the color trial lens will be placed closer to the patient's eyes than the UV trial lens. In one embodiment, the selected lenses are added from the back toward the eye. For example, the second color trial lens selected is placed in front of (or closer to the patient's eye) than the first selected color trial lens or UV trial lens.

The physician selection process therefore determines which color groups and which specific densities of the trial lenses in each color group that result in improvement in terms of visual function and visual performance. For example, blue may be selected over yellow based on the patient's responses and the physician observed improvements in the patient's visual function or performance.

At block 414, whether an UV trial lens was previously selected is determined. If an UV trial lens was previously selected, block 416 is performed. If an UV trial lens was not previously selected, block 424 is performed.

In one embodiment, if an UV trial lens was previously selected prior to a colored trial lens, then the choice for or against the UV trial lens should be challenged. This may include the density of the UV trial lens selected. Consequently, the physician removes the UV trial lens and compares the color trial lens with and without the UV trial lens of each density. For example, a selected color trial lens is compared with UV trial lenses of #1 density, #2 density, and #3.

At block 416, the UV trial lens is removed.

At block 418, whether there is an improvement in visual function is determined with and without an UV trial lens. If there is an improvement, block 420 is performed. If there is not an improvement, block 422 is performed.

Based on the clinical observations and the patient's improvement or enhancement of vision, the physician determines both the need for and the particular density of the UV trial lens to be selected as one of the component frequencies or wave lengths of light included or excluded from the refraction or neurochromatic prescription.

At block 420, the UV trial lens is removed from the selected trial lenses. For example, the UV trial lens may be removed from the holding mechanism of a neurochromatic refractor. In one embodiment, the UV trial lens is returned to the trial lens kit.

At block 422, the UV trial lens is returned to the holding mechanism because the UV trial lens improves visual function.

At block 424, reevaluation for UV trial lens is performed. For example, a patient, who previously did not select an UV trial lens, is checked for improvement with UV trial lenses. In one embodiment, the UV trial lens of each density are tested one at time in the neurochromatic refractor at the furthest position from the patient's eyes. The physician and patient continue to execute and rely upon the same clinical standards of measurement of visual acuity, visual ease and comfort, performance, and enhancement as the clinical criteria for including an UV trial lens as one of the prescriptive elements of the neurochromatic prescription. It is appreciated that it is not uncommon for a patient who has not selected an UV trial lens to select one. Similarly, it is appreciated that it is not uncommon for the UV trial lens to be rejected at the end of the prescriptive process.

At block 426, whether any colors (e.g., color groups) remain to be tested is determined. If colors remain, block 428 is performed. If there are no other colors to be tested, block 430 is performed.

At block 428, a next color is selected. In one embodiment, the next color group selected is based on an ordering of the trial lens kit.

At block 430, the neurochromatic prescription based on the trial lens selected is recorded. In one embodiment, the prescriptive process is complete when a patient accepts the a trial lens or lenses and the addition of another trial lens compromises or make difficult the patient's visual acuity, visual performance, visual function, or there is a notable reduction of the patient's visual performance. That is, a neurochromatic prescription may be complete when visual performance and enhancement cannot be improved by the addition of other trial lenses.

In one embodiment, any one of a plurality trouble shooting strategies may be undertaken by a physician during the prescriptive process. It is noted that in approximately 10% of the time a patient and physician may be unable to determine the benefit by comparison between any two of the physician selected neurochromatic trial lenses. It is noted that this is not of concern as the manufactured neurochromatic trial lenses do not individually or in collection with other trial lenses combine to articulate a neurochromatic prescription to exemplify each and every color or hue that effect the patient neurologically or neurophysiologically by impacting the patient's neurovisual processing within the brain itself.

A variety of strategies may be used to accomplish a more thorough exposure to more of the visual and non-visual spectrum to which the patient may respond favorably. These strategies may include: 1) varying the hue, intensity, or density (e.g., darkness of color) of the selected trial lenses, 2) changing the order of the initial neurochromatic trial lens prescription, 3) eliminating one or more of the initially selected trial lens (e.g., when there are three or more lenses within the prescription itself), 4) prescribing a slight modification to one or more of trial lenses, and 5) an overt challenge to a pre-existing ophthalmic prescription.

Changing the hue, density, color: If a patient has undistinguishable differentiation between any two of the trial lenses, by increasing each of the two trial lenses up the next highest density or color (e.g. up from a #1 to a #2, or up from a #2 to a #3), then a patient and physician can observe whether there is a benefit for each hue, density, or color.

In one embodiment, if the patient has selected a second or third level density trial lens (e.g., #2 or #3), by reducing the density of that selected trial lens, or all of the second or third preselected lenses may make it possible for the patient to select the appropriate trial lens. The increased or decreased density lenses may then be inserted into the neurochromatic refractor device for testing and the prescriptive process continued thereby resolving the dilemma of a choice between any two of the trial lenses. The increased or decreased density trial lens should be inserted in place of the trial lens being replaced to maintain the ordering of trial lenses.

Changing the order in which the trial lenses were selected: Patient and physician selections of neurochromatic trial lens may result in patients being confused by dysfunctions of general photophobia and neurovisual processing disorders. A patient may experience immediate comfort which may cause the patient and physician to initially choose the wrong trial lens. This may be due to selection of comfort over pathology. For example, the absence of eye strain may favorably alter a patient's pupil shape and be confusing for the physician. The cause of this may be that the resulting comfort the patient is experiencing is a result of the pathology to a frequency of light which has been detrimentally affecting neurovisual processing and thereby causing the symptoms. Though trial and error, with the exception of the UV trial lens, changing the order of the trial lens prescriptions and determining the results favoring the more functional or enhanced vision in each altered order of the initial trial lens selection or prescription may then be performed. The examination and prescription process may then be continued in the order determined.

Eliminating one or more of the previous neurochromatic trial lenses: Patients who present with multiple neurovisual and neurovisual processing disorders, symptoms or syndromes, are most commonly severely photophobic. Thus, darkness of any kind provides relief to such patients. For the physician this is problematic because symptoms, syndromes, and disorders often camouflage each other, thereby making it difficult to clinically differentiate. This may lead to these patients being prescribed multiple trial lenses of greater density.

However, once darkness is accomplished addressing most likely photophobia of a more general sort versus wave-length or frequency specific photophobia, the selection of more specific trial lenses is now possible. In one embodiment, upon the patient reporting that a trial lens is too dark or observes a tint when looking through the trial lens onto a white surface, there are two options: 1) reduce the density or hue of any trial lenses that do not exemplify a base trial lens (e.g., #1 trial lens) which has previously been prescribed or 2) completely eliminate any one of the trial lenses within the prescriptive formula choosing from the selection the specific trial lens for which the patient will denote a color or hue on a white surface during the examination and prescriptive process.

Increasing or decreasing the predetermined trial lens selected: Some patients may require increased darkness or hue while some patients will require less darkness or hue than in the trial lenses. Patients needing increased darkness or hue may be prescribed a quarter gradient. For example, if blue #1 is insufficient while blue #2 is an over prescription (e.g., seeing color or tint on white object), the prescription could be blue #1+50%. Similarly, if blue #1 is an over prescription, the prescription could be blue #1-50%.

Challenge an ophthalmic prescription: Due to the complexity of visual systems, the natures and pathologies of some patients, the ophthalmic prescription may be in error. Such an error is frequently a manufacturing error not congruent with a physician's orders. It is also possible that the physician did a "best guess" ophthalmic prescription. An ophthalmic prescription in error will likely negatively impact the ability to make an accurate neurochromatic prescription.

In one embodiment, the following three strategies may be performed. First, the ophthalmic prescription may be checked and verified for manufacturing error at another manufacturing laboratory other than the one which manufactured the lenses. If an error is found, the lenses may be remanufactured matching the physician's prescription.

Second, to the extent possible the closest neurochromatic prescription may be determined. A completely accurate neurochromatic prescription may not be possible because the ophthalmic prescription is not accurate. However, using the neurochromatic prescription in front of the patient's eyes and another ophthalmic refractive examination may be performed. If there are ophthalmic changes, which may be common, another neurochromatic prescription process may then be performed when a more correct and altered ophthalmic prescription can be worn by the patient.

Third, in some cases a patient's neurovisual processing is so negatively effected by the light that a physician cannot determine an appropriate nor accurate ophthalmic prescription. In such a case, a neurochromatic resultant lens may be made prior and worn during the standard ophthalmic examination. Generally, the physician will be able to more readily and accurately determine a standard ophthalmic prescription by having the patient view through the trial lens with the patient holding the selected trial lens in place. After the ophthalmic prescription is prescribed, the neurochromatic prescription may be removed and the neurochromatic prescription redone. It is expected that the neurochromatic prescription will be different.

It is appreciated that protection from an over-prescription should be quickly undertaken. Over-prescription may manifest as a compromised vision including making visual function blurry. Procedures to protect from over-prescription may include:

Visual performance and function have been improved by assessing before and after criteria established by pre-existing symptoms and syndromes therapeutically address by the prescribed neurochromatic lenses.

White appears white while colors become more distinct, more bold, with notable improvements in contrast sensitivities noted and treated with neurochromatic lenses. White may appear to a patient as very slightly "shaded." In other words, abnormally higher amounts of "glare" have been neurochromatically altered by the neurochromatic trial lens.

Improvements in saccade should be noted. There will be increased ease in sight recognition, reading speed, and flow while a patient is wearing the neurochromatic lenses as compared to not wearing the neurochromatic lenses.

Patients should have a measurable increase in visual performance and function at all distances with the resultant prescribed neurochromatic lenses as compared to the same viewing without the neurochromatic lenses. Patients should have a measurable increase in their visual fields as a result of wearing the resultant prescribed neurochromatic lenses as compared to the same determination without the wearing of the prescribed neurochromatic lenses.

Longstanding conditions, symptoms, syndromes, complications (e.g., cerebral hemorrhage, strokes, brain swelling, and reduced consciousness) will frequently respond favorably to trial lens and neurochromatically prescribed lenses. The observation in terms of positive changes within the patient may take days or weeks. It is noted that since neurochromatic lenses are a noninvasive therapeutic intervention, little if any harm can be done. It is appreciated that many patients have dramatic improvements through the use of neurochromatic prescriptive lenses.

Figure 5A:
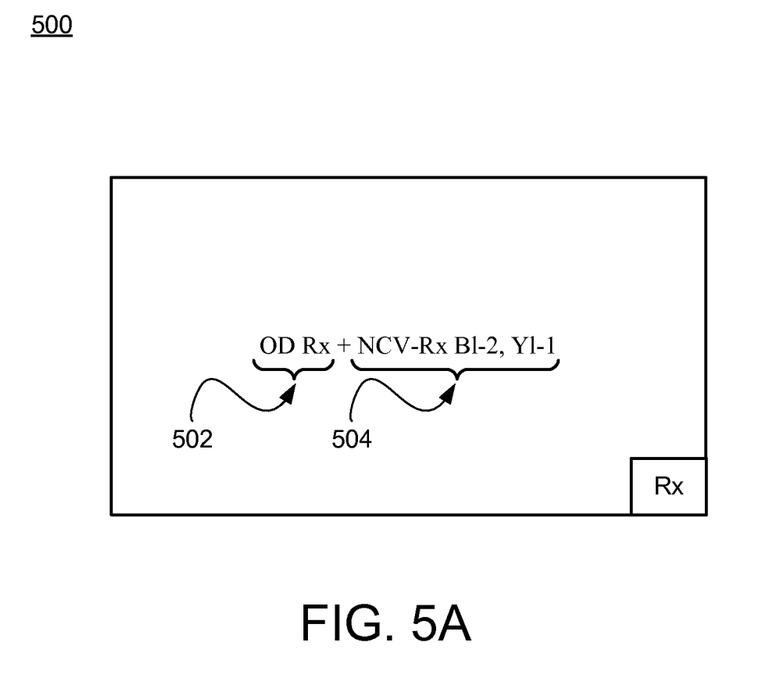
FIG. 5A-B show exemplary neurochromatic prescriptions in accordance with embodiments of the present invention.
Figure 5B:
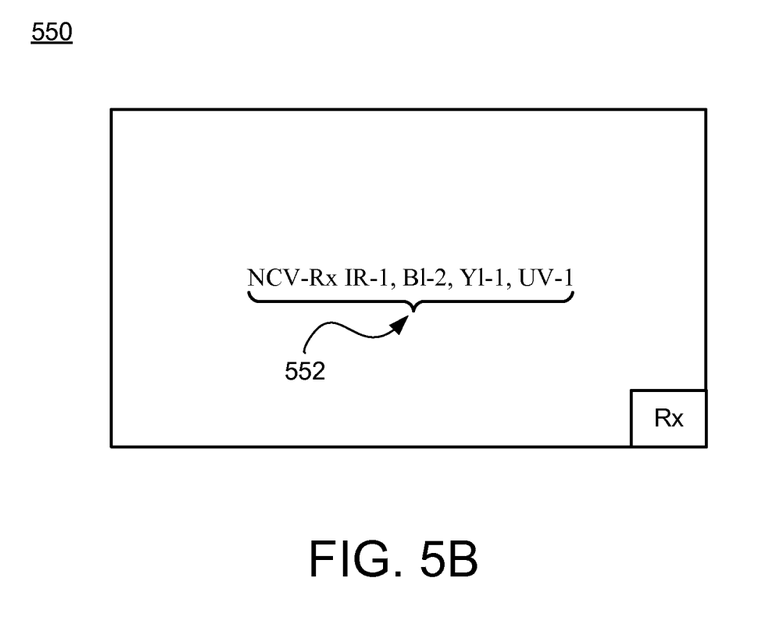

FIG. 5A-B show exemplary neurochromatic prescriptions in accordance with embodiments of the present invention. FIG. 5A shows an exemplary prescription 500 comprising ophthalmic prescription 502 and neurochromatic prescription 504. Ophthalmic prescription 502 may be a conventional ophthalmic prescription (e.g., for near-sightedness or far-sightedness). Neurochromatic prescription 504 comprises NVC-Rx B1-2, Y1-1 which indicates that the patient needs a lens with blue of #2 density or frequency or wavelength and yellow of #1 density.

FIG. 5B shows an exemplary neurochromatic prescription 550. Prescription 550 may be for a patient who has normal vision (e.g., does not need an ophthalmic prescription) but can benefit from neurochromatic lenses. Prescription 550 includes neurochromatic prescription 552 which comprises NVC-Rx IR-1, B1-2, Y1-1, UV-1 which indicates that the patient needs a lens with infrared of #1 density or frequency or wavelength, blue of #2 density, yellow of #1 density, and UV of #1 density.

Lenses may then be manufactured in accordance with the order of the prescription. The trial lenses that are selected correspond to the layers of the resultant lens and reflect the order of lens saturation. In one embodiment, the order is a contingent component in the manufacturing process. In one embodiment, the resultant lens material is heated and dyed with a first frequency or wavelength, bleached back, and then dyed with a second frequency or wavelength. The heating allows for some expansion and facilitates increased absorption of the dyes. The amount of time and the temperature impact the lens darkness. In one embodiment, a resultant lens based on the prescription has an intermingling (or saturation) of the adjacent dyes. For example, a resultant lens having Blue #1 and Yellow #2 would have a region of intermingling of blue #1 and Yellow #2.

The foregoing descriptions of specific embodiments of the present invention have been presented for purposes of illustration and description. They are not intended to be exhaustive or to limit the invention to the precise forms disclosed, and many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the claims appended hereto and their equivalents.

What is claimed is:

1. A method for determining a lens prescription, said method comprising:
    selecting a first ultraviolet (UV) trial lens and a second UV trial lens;
    determining whether said first UV trial lens or said second UV trial lens results in greater improvement in visual function;
    selecting said second UV trial lens for said prescription when said second UV trial lens results in greater improvement in visual function as compared to said first UV trial lens;
    selecting a first color group comprising a first color trial lens and a second color trial lens;
    determining whether said first color trial lens or said second color trial lens results in greater improvement in visual function;
    selecting said second color trial lens for said prescription when said second color trial lens results in greater improvement in visual function as compared to said first color trial lens;
    selecting a second color group comprising a third color trial lens and a fourth color trial lens;
    determining whether said third color trial lens or said fourth color trial lens results in greater improvement in visual function; and
    selecting said fourth color trial lens for said lens prescription when said fourth color trial lens results in greater improvement in visual function as compared to said third color trial lens.

2. The method of claim 1 further comprising:
    activating a full spectrum lighting element.

3. The method of claim 1 further comprising:
    activating a camera operable to record said improvement in visual function.

4. The method of claim 3 wherein said camera is operable to record a pupillary response to said first color trial lens.

5. The method of claim 1 wherein said color group comprises a third color trial lens and said method further comprises:
    determining whether said second color trial lens or said third color trial lens results in greater improvement in visual function; and
    selecting said third color trial lens for said lens prescription when said third color trial lens results in greater improvement in visual function as compared to said second color trial lens.

6. The method of claim 1 further comprising:
    selecting a first infrared (IR) trial lens and a second IR trial lens;
    determining whether said first IR trial lens or said second IR trial lens results in greater improvement in visual function;
    selecting said second IR trial lens for said lens prescription when said second IR trial lens results in greater improvement in visual function as compared to said first IR trial lens.

7. The method of claim 1 further comprising:
determining whether removal of said second UV trial lens results in an improvement in visual function.

8. The method of claim 1 further comprising:
reevaluating said second UV trial lens for improvement in visual function after determining improvement in visual function with a plurality of color trial lenses from a plurality of color groups.

9. A method for selecting a color lens for a prescription, said method comprising:
selecting a color group comprising a plurality of color trial lenses; selecting a first color trial lens of said plurality of color trial lenses corresponding to a first wavelength of light;
determining if there is a first improvement in visual function with said first color trial lens;
in response to said first improvement in visual function, selecting a second color trial lens corresponding to a second wavelength of light;
determining if there is a second improvement in visual function with said second color trial lens;
in response to said second improvement in visual function, placing said second color trial lens into a holding mechanism operable to hold a plurality of trial lenses; and
recording said second wavelength of light into said prescription.

10. The method as described in claim 9 further comprising:
in response to not determining said second improvement in visual function, placing said first color trial lens into said holding mechanism.

11. The method as described in claim 9 further comprising:
in response to not determining said first improvement in visual function, selecting another color group.

12. The method as described in claim 9 wherein said color group is selected from the group consisting of red, orange, yellow, green, blue, indigo, and violet.

13. The method as described in claim 9 further comprising:
determining if there is a third improvement in visual function with said first color trial lens and said second color trial lens; and
in response to said third improvement in visual function, placing said first color trial lens and said second trial lens into said holding mechanism.

14. The method as described in claim 9 further comprising:
in response to said second improvement in visual function, selecting a third color trial lens corresponding to a third wavelength of light, wherein said third color trial lens is darker than said second color trial lens; and
determining if there is a third improvement in visual function with said third color trial lens;
in response to said third improvement in visual function, placing said third color trial lens into said holding mechanism; and
in response to not determining said third improvement in visual function, placing said second color trial lens into said holding mechanism.

15. A method for selecting a ultraviolet (UV) trial lens for a prescription, said method comprising:
selecting a first UV trial lens of a plurality of UV trial lenses corresponding to a first wavelength;
determining if there is a first improvement in visual function with said first UV trial lens;
in response to said first improvement in visual function, selecting a second UV trial lens corresponding to a second wavelength;
determining if there is a second improvement in visual function with said second UV trial lens;
in response to said second improvement in visual function, placing said second UV trial lens into a holding mechanism operable to hold a plurality of trial lenses; and
recording said second wavelength into said prescription.

16. The method of claim 15 further comprising:
in response to not determining said second improvement in visual function, placing said first UV trial lens into said holding mechanism.

17. The method of claim 15 further comprising:
in response to not determining said first improvement in visual function, selecting a first color trial lens.

18. The method of claim 16 further comprising:
determining if there is a third improvement in visual function with said first UV trial lens and said second UV trial lens; and
in response to said third improvement in visual function, placing said first UV trial lens and said second trial lens into said holding mechanism.

19. The method of claim 15 wherein said method further comprises:
in response to said second improvement in visual function, selecting a third UV trial lens corresponding to a third wavelength; and
determining if there is a third improvement in visual function with said third UV trial lens;
in response to said third improvement in visual function, placing said third UV trial lens into said holding mechanism; and
in response to not determining said third improvement in visual function, placing said second UV trial lens into said holding mechanism.

\* \* \* \* \*